(12) United States Patent
Christy

(10) Patent No.: US 8,016,769 B2
(45) Date of Patent: Sep. 13, 2011

(54) RETRACTABLE NEUROSENSORY EVALUATION TOOL

(76) Inventor: George M. Christy, Lincoln, CA (US)

( * ) Notice: Subject to any disclaimer, the term of this patent is extended or adjusted under 35 U.S.C. 154(b) by 499 days.

(21) Appl. No.: 12/231,137

(22) Filed: Aug. 29, 2008

(65) Prior Publication Data

US 2010/0056949 A1 Mar. 4, 2010

(51) Int. Cl.
*A61B 19/00* (2006.01)
(52) U.S. Cl. .......................................... 600/557
(58) Field of Classification Search ............... 600/557, 600/587, 592, 553; D24/142
See application file for complete search history.

(56) References Cited

U.S. PATENT DOCUMENTS

| | | | |
|---|---|---|---|
| 3,185,146 A * | 5/1965 | Leopoldi | 600/553 |
| 3,662,744 A | 5/1972 | Low | |
| 5,437,288 A | 8/1995 | Schwartz | |
| 5,443,907 A | 8/1995 | Slaikeu | |
| 5,492,132 A | 2/1996 | Weinstein | |
| 5,542,434 A | 8/1996 | Imran | |
| 5,582,619 A | 12/1996 | Ken | |
| 5,823,969 A | 10/1998 | Christy | |
| D439,336 S * | 3/2001 | Najmi | D24/142 |
| 6,196,976 B1 | 3/2001 | Christy | |
| 6,234,976 B1 | 5/2001 | Linden | |
| 6,234,977 B1 | 5/2001 | Christy | |
| D489,455 S * | 5/2004 | Mork | D24/142 |
| 2008/0097236 A1 | 4/2008 | Kuban | |

* cited by examiner

*Primary Examiner* — Max Hindenburg
*Assistant Examiner* — Brian Szmal
(74) *Attorney, Agent, or Firm* — Heisler & Associates

(57) ABSTRACT

The tool is an instrument including a filament which is brought into contact with an individual to test sensory perception of the individual. When the filament resiliently buckles a standard force is applied to the individual. The filament is retractable within a housing. The filament is mounted upon a shuttle which moves relative to the housing to position the filament either in a stored position within an interior chamber of the housing or in a deployed position outside of the housing. The filament both translates and rotates to move from the stored position to the deployed position. The instrument is configured to securely hold the filament in both the stored position, where the filament is kept safe when not in use, and a deployed position, where the filament is held firm during use of the filament for sensory perception testing.

18 Claims, 6 Drawing Sheets

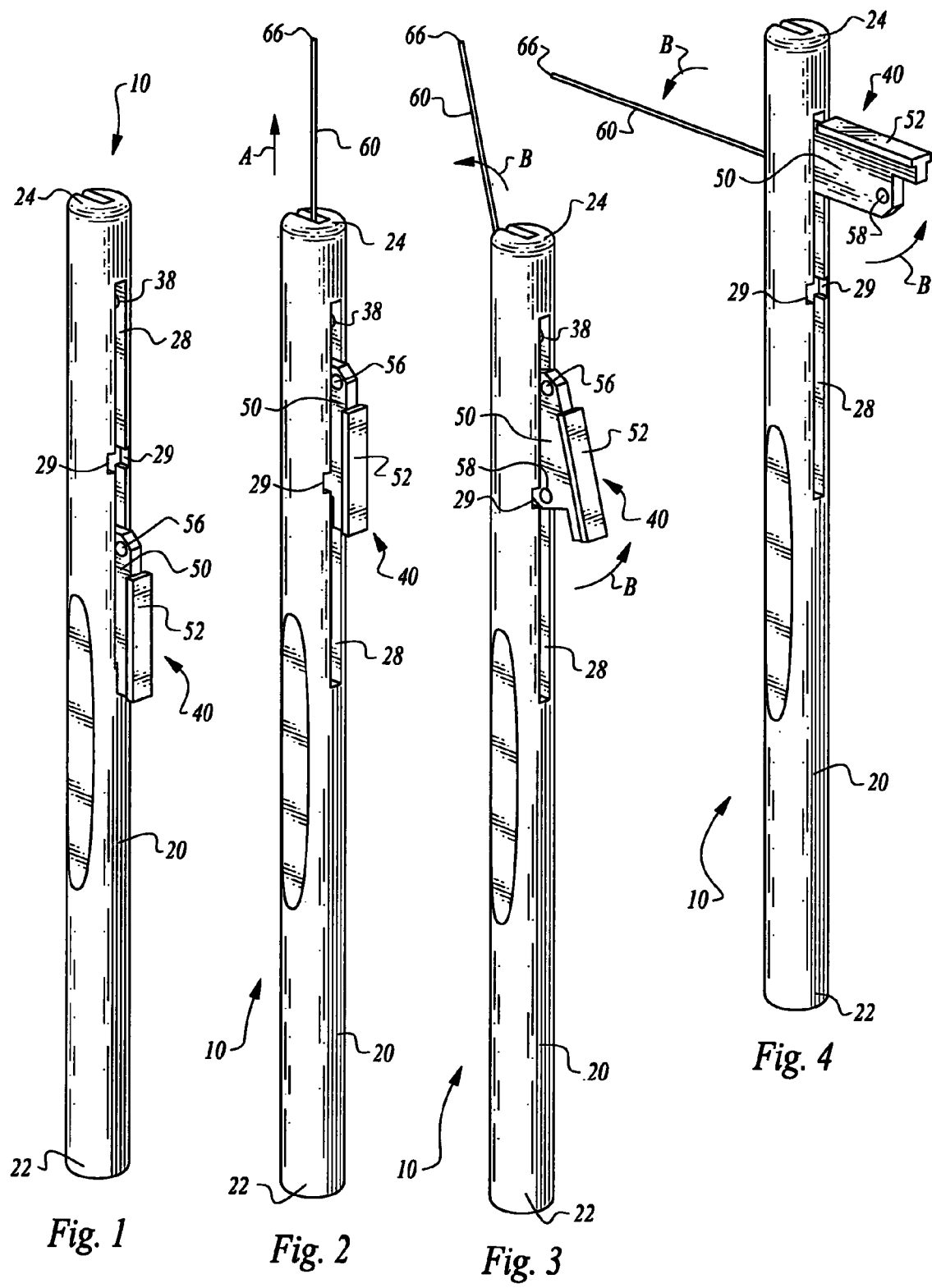

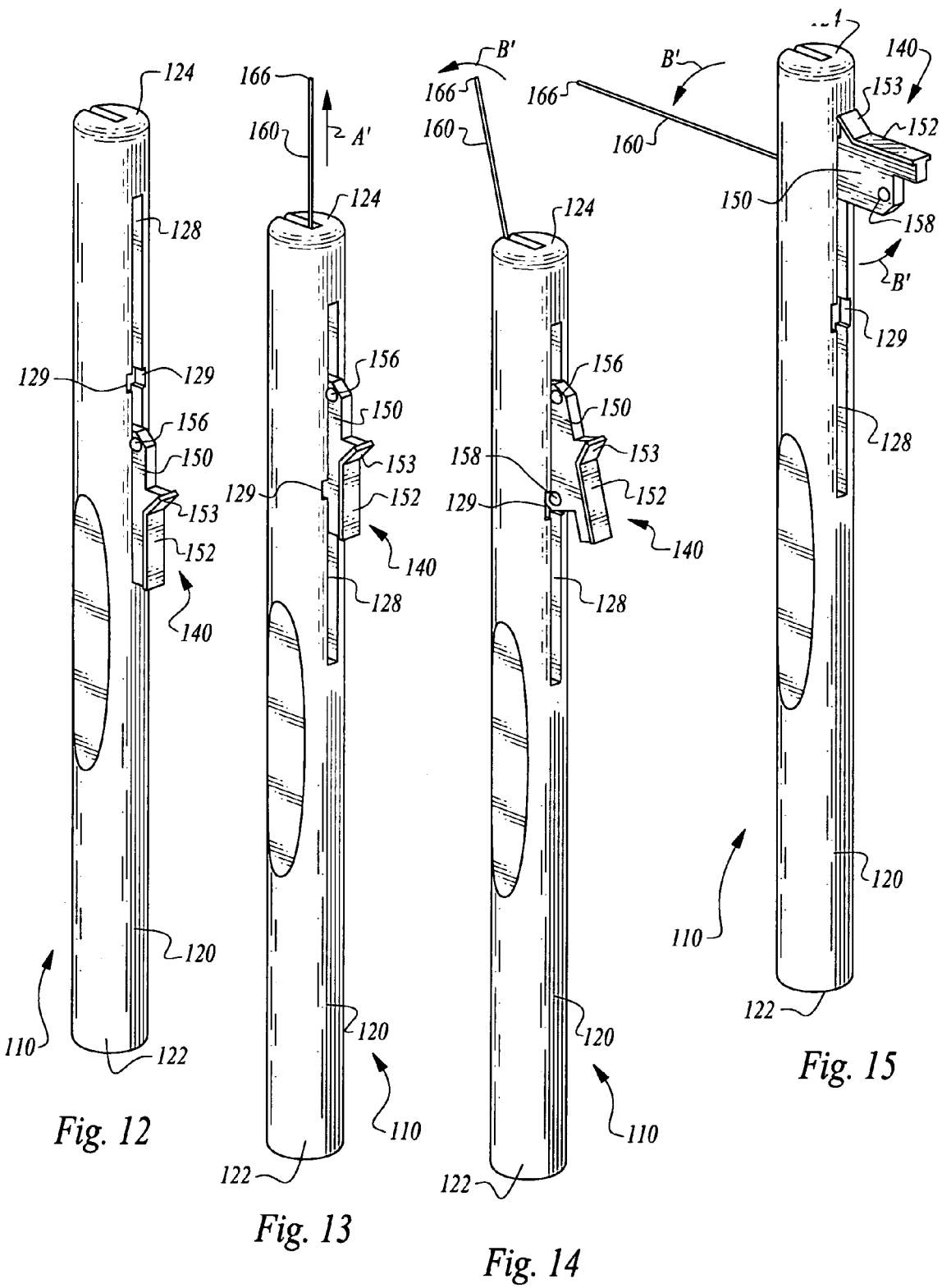

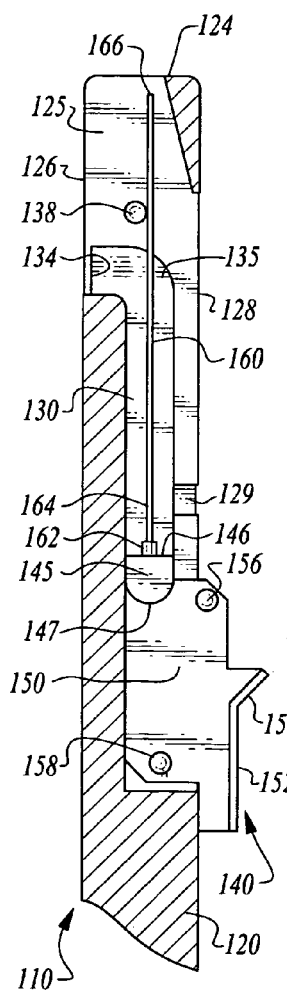
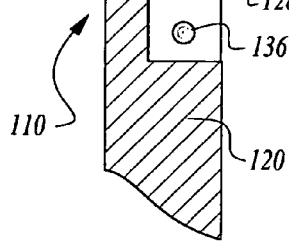
Fig. 19
Fig. 20
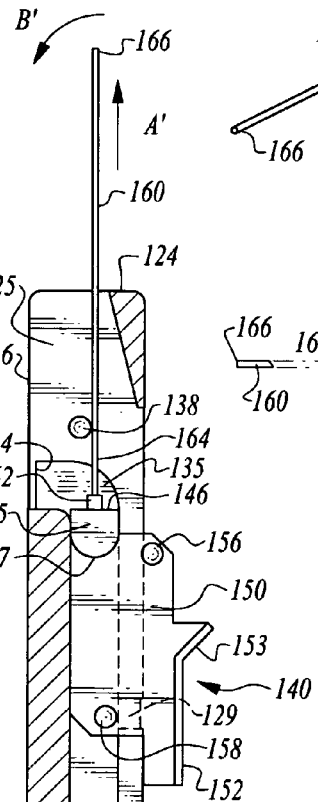
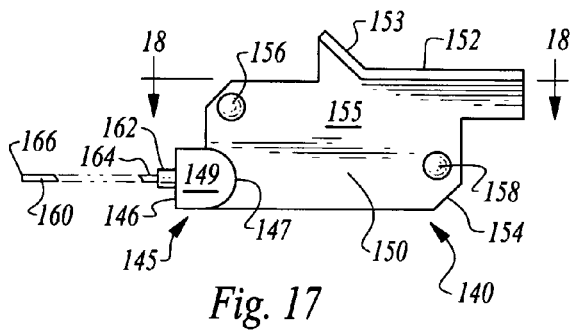
Fig. 16
Fig. 17
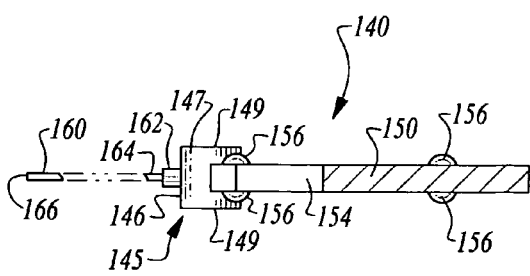
Fig. 18

RETRACTABLE NEUROSENSORY EVALUATION TOOL

FIELD OF THE INVENTION

The following invention relates to medical instruments used in evaluating the health of nerves in or near the skin. More particularly, this invention relates to neurosensory evaluation tools which utilize a filament which buckles when a predetermined force is applied so that the tool can apply a repeatable standard force (and pressure) to the skin of an individual undergoing evaluation.

BACKGROUND OF THE INVENTION

Some medical conditions have as a symptom or detrimental effect loss or reduction of tactile sensitivity of the skin of the individual. Often such medical conditions result in loss of tactile sensory perception over a period of time rather than abrupt loss of touch sensitivity. Thus, it is beneficial to have instruments which can measure the tactile sensitivity of the individual with sufficient accuracy to be able to track the tactile sensitivity of the individual over time and compare tactile sensitivity of the individual to other individuals exhibiting the same or related conditions.

One general category of tactile sensory instrument known in the art is an elongate monofilament or similar resilient elongate flexible structure which can be forced axially against the skin of the individual until the filament buckles. The filament is designed to always apply substantially the same force before the filament buckles. The filament is sufficiently elastic that when the load is removed the filament returns to its original orientation. The filament is of a type which provides a maximum force before buckling. Thus, if the user of the instrument applies the filament against the skin with too much force, it will still buckle when this maximum force is exerted on the instrument, so that the instrument never applies a force greater than this threshold force to the skin of the individual.

If the individual can feel this force (also quantifiable in terms of pressure) such tactile sensitivity can be noted in the individual's file. Various different body parts, and particularly extremities of the individual can be tested in this way and records gathered. Different testing instruments having different filaments with different threshold forces before buckling can be utilized to determine the point at which the individual no longer has sufficient tactile sensitivity to feel the loads applied by the device.

Examples of such prior art systems include U.S. Pat. Nos. 3,662,744 and 5,492,132. Prior art filament based tactile sensory perception monitoring tools benefit from having the filament be protected in some way when not in use. The filament can become damaged when merely placed in a pocket of a user or otherwise left exposed. Once the filament has been damaged it is no longer applying the proper force before buckling and so can lead to poor data being collected. Prior art filament based tactile sensory instruments have been provided by the inventor to provide such filament protection as well as systems for controlling an amount that the filament extends from a housing for application of a variable force (or pressure). Examples of such devices include U.S. Pat. Nos. 5,823,969, 6,196,976 and 6,234,977. While such retractable tactile sensory instruments have addressed the problem of protecting the monofilament to some extent, the filament remains in a position where it can catch on a shirt pocket or other holder when being stored because the filament is only re-positioned through a pivoting motion partially out of danger of potential contact and damage to the filament.

The problem of filament damage cannot be overemphasized. Often the filament can be bent or otherwise damaged in a manner which is substantially imperceptible visually or in use of the instrument. Thus, the instrument appears to be completely functional and accurately calibrated to apply the expected force. In reality, such an instrument that has been slightly damaged can be applying an improper lower or higher force (most typically lower), leading to improper diagnosis. Accordingly, a need exists for a tactile sensory evaluation instrument which has a filament that can be retracted in a manner which provides a high reliability that the filament will remain protected while retracted.

SUMMARY OF THE INVENTION

With this invention a retractable neurosensory evaluation tool is provided which is fully retractable so that the filament of the instrument is fully protected from inadvertent contact when in its retracted position. The instrument includes a housing which has an exterior which can be readily gripped by a user. An interior chamber is provided within the housing which contains a testing filament that can be stored therein when in a retracted position. A guide is provided within this interior chamber which has an elongate form. The filament is coupled to a body and the body includes a slide which slides along the guide from a stored position to a deployed position. Once the body is at the deployed position, the body can rotate to pivot the filament out of the interior chamber and into a position perpendicular to the long axis of the housing for use.

The rotation can occur by providing the guide with a curve near one end thereof or by configuring the body to both slide within the guide and pivot within the guide. In either embodiment the filament rotates from a stored position aligned within the interior chamber of the housing to a deployed position where it is pivoted (preferably to perpendicular to the housing) to position the filament where it can be effectively utilized.

OBJECTS OF THE INVENTION

Accordingly, a primary object of the present invention is to provide a tool for neurosensory evaluation involving bringing a filament of the tool into contact with skin of an individual.

Another object of the present invention is to provide an instrument which can provide an indication of the level of tactile sensitivity of the individual.

Another object of the present invention is to provide a tactile sensory instrument which is easy to use.

Another object of the present invention is to provide a tactile sensory instrument which has a filament which buckles when a threshold force is applied along a long axis of the filament and which filament is retracted for protection when the instrument is not in use.

Another object of the present invention is to provide a tactile sensory instrument which has a filament which is both translated linearly and rotated relative to a housing to move the filament from a stored position to a deployed position.

Another object of the present invention is to provide a neurosensory evaluation instrument which applies a uniform consistent force with repeated use.

Another object of the present invention is to provide a neurosensory evaluation instrument which avoids damage when stored or otherwise not in use to minimize the potential for damage to the instrument.

Other further objects of the present invention will become apparent from a careful reading of the included drawing figures, the claims and detailed description of the invention.

BRIEF DESCRIPTION OF THE DRAWINGS

FIGS. 1-4 are perspective views of the instrument of this invention following sequential steps in transition of a filament of the instrument from a stored position (FIG. 1) to a deployed position (FIG. 4).

FIGS. 12-15 are perspective views of an alternative instrument of that which is shown in FIGS. 1-11 and illustrating the sequential steps in transition of the filament from a stored position (FIG. 12) to a fully deployed position (FIG. 15).

FIG. 16 is a perspective view of a shuttle portion of the instrument of FIGS. 12-15 including the body and filament separate from the housing.

FIG. 17 is a side elevation view of that which is shown in FIG. 16.

FIG. 18 is a top plan sectional view taken along line 18-18 of FIG. 17, illustrating further details of the shuttle in the embodiment of FIGS. 12-15.

FIGS. 19-22 are side elevation full sectional views of portions of that which is shown in FIGS. 12-15 and illustrating interior details of the shuttle including the body and the filament during transition of the instrument from having the filament in a stored position to having the filament in a fully deployed position.

DESCRIPTION OF THE PREFERRED EMBODIMENT

Figure 8:
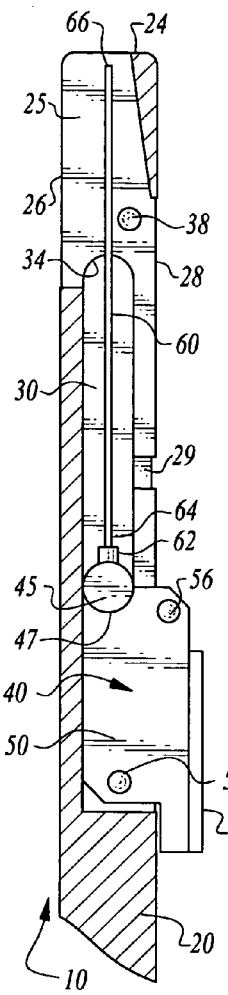
FIG. 8 is a side elevation sectional view of a portion of that which is shown in FIG. 1 to illustrate the shuttle and associated filament in a stored position within the housing.
Figure 9:
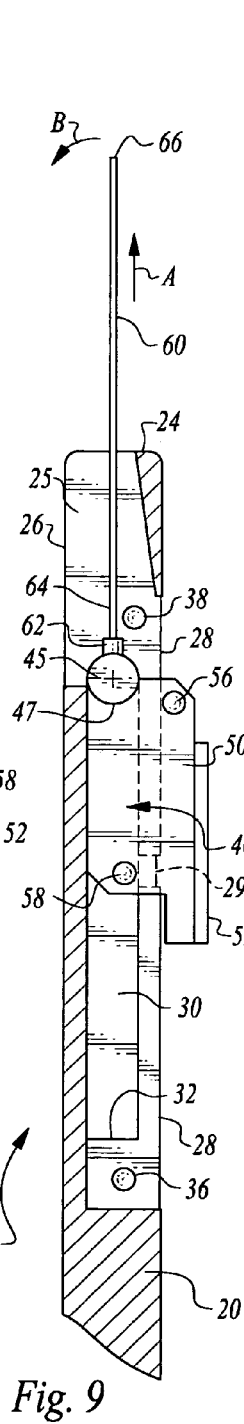
FIG. 9 is a side elevation sectional view of a portion of that which is shown in FIG. 2, showing the filament translated to a deployed position but before rotation thereof.

Referring to the drawings, wherein like reference numerals represent like parts throughout the various drawing figures, reference numeral 10 is directed to an instrument (FIGS. 1-4) for use in neurosensory evaluation. The instrument 10 has a filament 60 which buckles (FIG. 11) when a threshold force is applied axially thereto. This threshold force is substantially constant so that a consistent force is applied to an individual, such as to a finger F (FIG. 11) so that useful evaluation of tactile sensory perception of an individual can be provided. The filament 60 is retractable from a stored position inside an interior chamber 25 of a housing 20 to a deployed position both translating linearly out of the housing 20 and pivoting relative to the housing 20. When the filament 60 is in the retracted position within the interior chamber 25, the filament 60 is protected from damage.

In essence, and with particular reference to FIGS. 5-9, basic details of the instrument 10 are described according to a preferred embodiment. The instrument 10 generally includes two parts including a housing 20 (see also FIGS. 1-4) and a shuttle 40. The shuttle 40 moves relative to the housing 20 (arrows A and B of FIG. 9) to move the filament 60 from its stored position within the interior chamber 25 to its deployed position outside of the interior chamber 25.

The housing 20 includes tracks 30 within the interior chamber 25 which extend longitudinally along a long axis of the housing 20. The shuttle 40 includes a slide 45 which translates within the tracks 30. The shuttle 40 includes a body 50 coupled to the slide 45. The body 50 has at least a portion thereof which extends out of the interior chamber 25 so that a finger of the user or other structure can act on the body 50 to move the shuttle 40 and associated slide 45 along the tracks 30 within the interior chamber 25 of the housing 20.

The filament 60 is coupled to the body 50. The slide 45 is configured to allow rotation within the tracks 30. Thus, the shuttle 40 can both translate linearly along the tracks 30 and can also pivot about the slide 45 to rotate the filament 60 (about arrow B of FIG. 10) from a first position aligned with the long axis of the housing 20 to a second position preferably substantially perpendicular to the long axis of the housing 20.

An alternative embodiment instrument 110 is shown in FIGS. 12-22. The instrument 110 is similar to the preferred embodiment of FIGS. 1-11 except that tracks 130 rotate about a curve at one end thereof. A slide 145 is configured to rotate about this curve following the tracks 130, rather than pivoting about a single point.

More specifically, and with particular reference to FIGS. 1-4 and 8-11, particular details of the housing 20 are described according to the first embodiment instrument 10. The housing 20 is preferably an elongate rigid construct. The housing 20 can be formed from two separate halves that are then bonded together. Such forming can be by injection molding of a plastic (e.g. polyethylene) or other material. As an alternative, the housing 20 could be formed as a unitary mass of material. The housing 20 is preferably lightweight and substantially rigid in form. The housing 20 preferably has an elongate form similar to that of a pencil to allow it to be firmly grasped by fingers of a user. Such a size also allows for convenient storage and transport within a pocket, such as a shirt pocket of the user, when not in use. To this end, an exterior of the housing 20 preferably is substantially cylindrical in form and with optional continuous and surface details to allow for a solid finger grip of the housing 20.

The housing 20 includes a proximal end 22 and a distal end 24. The filament 60 is configured so that it is preferably retracted and deployed at the distal end 24 with the proximal end 22 being that end closest to the area on the housing 20 typically grasped by the user. The interior chamber 25 resides within the housing 20 between the proximal end 22 and the distal end 24. Most preferably, at least portions of the interior chamber 25 extend to the distal end 24.

The interior chamber 25 is accessed through both a front slot 26 and a rear slot 28. The front slot 26 allows the filament 60 to pivot out of the interior chamber 25 when being transitioned by rotation (along arrow B of FIGS. 9 and 10) from a stored position within the interior chamber 25 to a deployed position ready for use. The rear slot 28 provides a space through which portions of the body 50 supporting the filament 60 can pass such as to allow a finger of the user to act on the filament 60 to move the filament 60 from its retracted position within the interior chamber 25 to its deployed position.

The interior chamber 25 is shown in this embodiment as a generally of constant width and this width is similar to a width of the slots 26, 28. Alternatively, the interior chamber 25 can have a greater width than that of the slots 26, 28. Particular contours of the interior chamber 25 and slots 26, 28 are shown in FIGS. 8-11. While such a contour for the interior chamber 25 is shown, this contour of the interior chamber 25 could be altered to accommodate design choices of one practicing this invention.

With particular reference to FIGS. 8-11, details of the tracks 30 within the interior chamber 25 of the housing 20 are described, according to this embodiment. The tracks 30 provide a preferred form of guide for guiding the slide 45 from the stored configuration within the interior chamber 25 to a deployed configuration for the instrument 10. A pair of these tracks 30 are preferably in the form of recesses formed in side walls of the interior chamber 25. These recesses are preferably of substantially constant depth extending from a first end 32 closest to the proximal end 22 to a second end 34 closest to the distal end 24. In this embodiment the tracks 30 extend linearly from the first end 32 to the second end 34.

Preferably, the first end 32 is square and the second end 34 is rounded. As can be seen in FIGS. 8-11, the tracks 30 support the slide 45 of the shuttle 40 moving there along. In particular, the slide 45 moves from a stored position closer to the first end 32 to the second end 34, but spaced somewhat from the first end 32. When the shuttle 40 is transitioned to the deployed position, the slide 45 moves to the second end 34. By configuring the second end 34 to have a circular cross-section, and configuring the slide 45 to have a cylindrical surface 47, the shuttle 40 can pivot about the slide 45 (arrow B of FIGS. 9 and 10) when the slide 45 is abutting the second end 34 of the tracks 30.

Most preferably, the rear slot 28 on the housing 20 includes notches 29 therein at a midpoint thereof. These notches 29 define a portion of the rear slot 28 which is slightly wider than other portions of the rear slot 28. These notches 29 can serve various different purposes such as providing a place through which the slide 45 can be passed through the rear slot 28 to install the shuttle 40 within the interior chamber 25 of the instrument 10 during initial assembly. Also, the notches 29 provide a space through which humps 56, 58 on the body 50 of the shuttle 40 can pass when the shuttle 40 is rotating (about arrow B of FIGS. 9 and 10).

Most preferably, a first dimple 36 pair are located near the first end 32 of the tracks 30. A second dimple pair 38 is preferably located just past the second end 34 of the tracks 30. These dimples 36, 38 are preferably in the form of concave spherical recesses extending partially into the side walls of the interior chamber 25 of the housing 20. These dimples 36, 38 receive the humps 56, 58 to hold the shuttle 40 either in the stored position with the filament 60 safely within the interior chamber 25 of the housing 20 or in the deployed position preventing accidental retraction of the shuttle 40 when the filament 60 is being applied to skin of an individual. The humps 56, 58 and dimples 36, 38 could be swapped for each other as an alternative, but most preferably have the arrangement depicted. Humps 58 are positioned such that they slide along an inside wall of the chamber 25 adjacent the rear slot 28 to prevent premature pivoting of the shuttle 40, in a manner that might otherwise cause damage to the filament 60.

Figure 5:
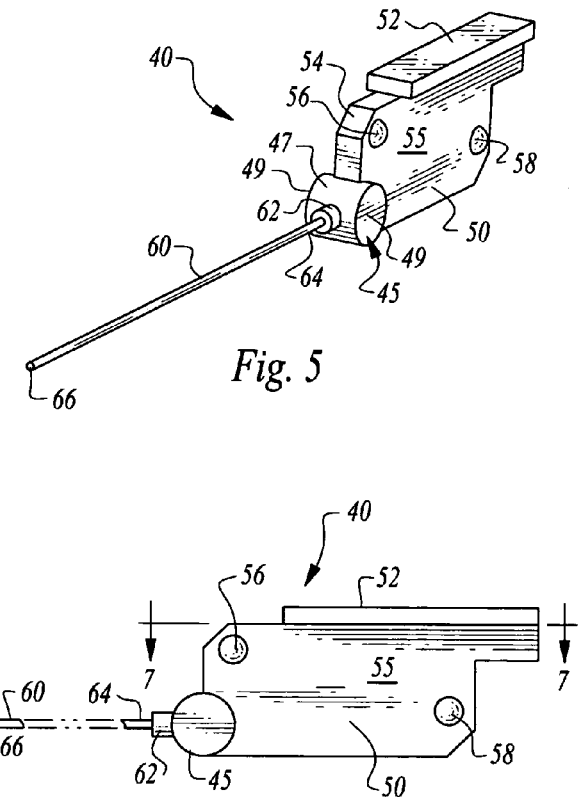
FIG. 5 is a perspective view of a shuttle portion of the instrument shown alone.
Figure 6:
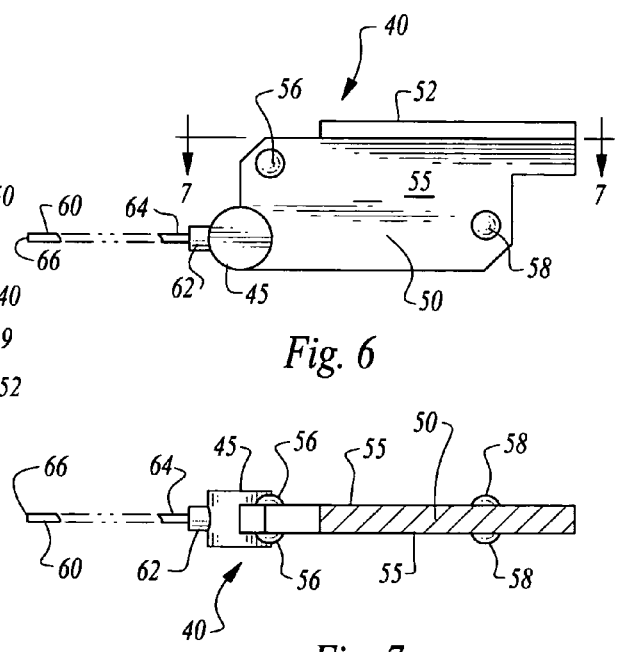
FIG. 6 is a side elevation view of the shuttle shown in FIG. 5.
Figure 7:
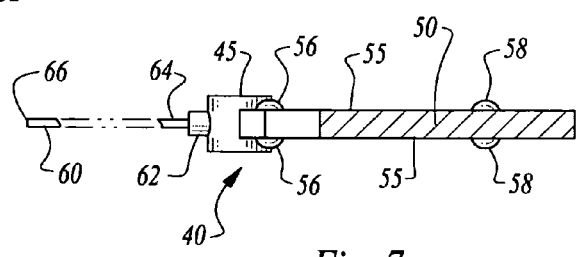
FIG. 7 is a top plan full sectional view of the shuttle shown in FIG. 5, taken along lines 7-7 of FIG. 6.
Figures 10, 11:
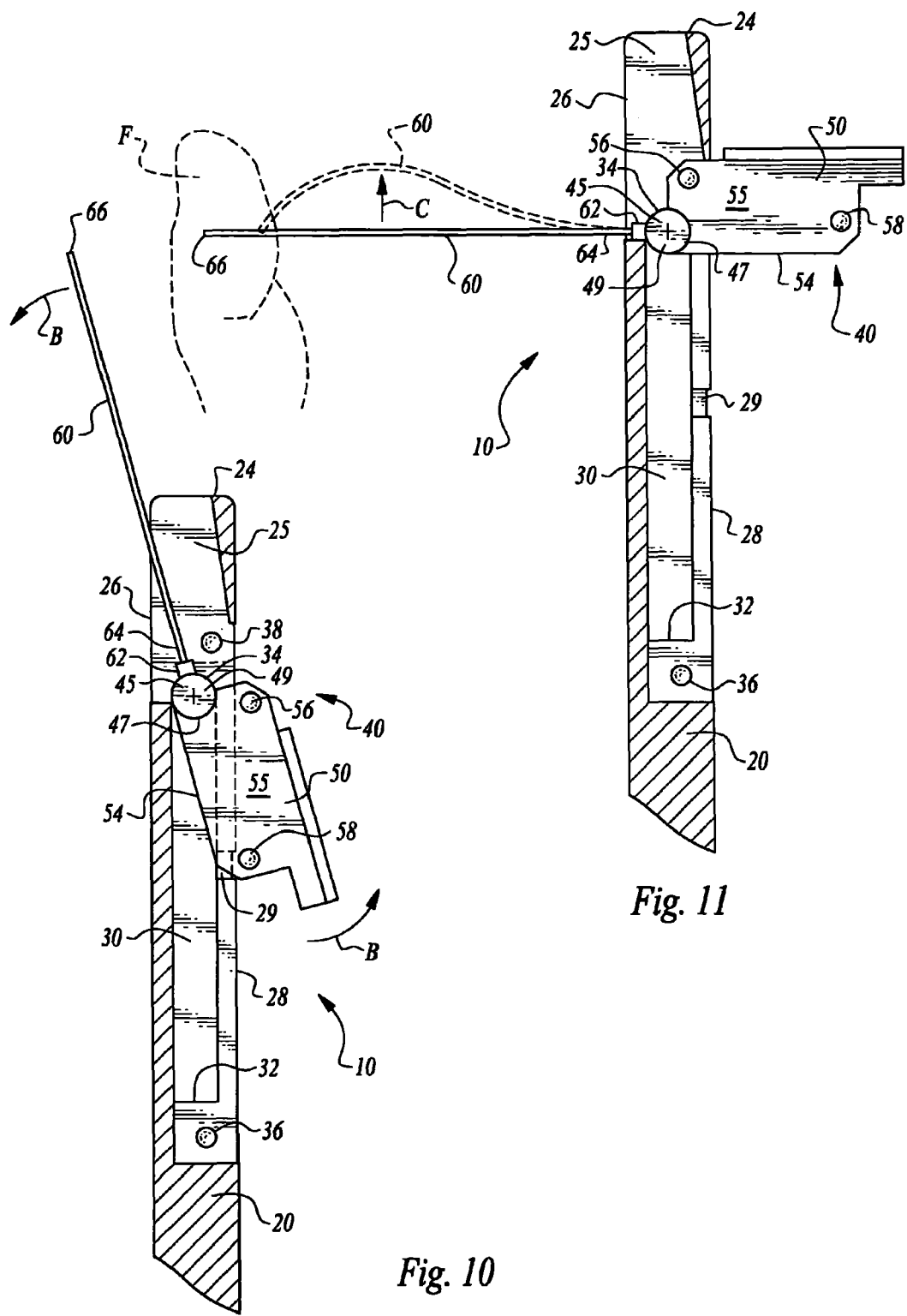
FIG. 10 is a side elevation sectional view of a portion of that which is shown in FIG. 3 and with the filament undergoing rotation toward a final deployed position.
FIG. 11 is a side elevation sectional view of a portion of that which is shown in FIG. 4 after full deployment and rotation of the filament thereof. The filament is shown both before and after (in broken lines) coming into contact with a finger of an individual and illustrating how the filament buckles when a threshold force is applied.

With particular reference to FIGS. 5-7, details of the shuttle 40 and associated structures are described, according to this preferred embodiment. The shuttle 40 defines a preferred form of second portion of the instrument 10 which moves relative to the housing 20 to move the filament 60 from this stored position within the interior chamber 25 to the deployed position ready for use outside of the housing 20 (FIG. 11). The shuttle 40 thus includes the slide 45, body 50 and filament 60.

The slide 45 is preferably in the form of a cylindrical structure with the cylindrical surface 47 and flat ends 49. The cylindrical surface 47 preferably has a diameter similar to a width of the tracks 30. The flat ends 49 reside within the tracks 30. The slide 45 thus allows the shuttle 40 to both translate and rotate relative to the tracks 30.

The slide 45 is preferably rigidly formed along with the body 50 from a monolithic mass of material, such as injection moldable plastic (e.g. polyethylene). The body 50 includes a lever 52 which is positioned to reside outside of the rear slot 28 of the housing 20. An edge 54 defines a periphery of the body 50 to which both the lever 52 and slide 45 are attached. Sides 55 define lateral sides of the body 50 and preferably are generally parallel with each other to define a constant width for the body 50.

The edge 54 of the body 50 has a contour which generally keeps the shuttle 40 from being able to rotate except when the slide 45 has been positioned adjacent the second end 34 of the tracks 30. The lever 52 is preferably positioned most distant from the slide 45 to keep the lever 52 from interfering with the housing 20 and abutting the rear slot 28 when the shuttle 40 rotates (about arrow B of FIGS. 9 and 10) to move the shuttle 40 to the deployed position.

The body 50 also preferably includes a pair of the forward humps 56 and a pair of the rearward humps 58 extending laterally from the sides 55. These humps 56, 58 are preferably convex spherical raised portions of the body 50 which have a diameter and size similar to that of the dimples 36, 38 within the interior chamber 25 of the housing 20. The pair of rearward humps 58 reside within the pair of first dimples 36 when the shuttle 40 is in the stored position. When the shuttle 40 is slid linearly (along arrow A of FIG. 9) the rearward humps 58 come out of the first dimples 36.

The pair of forward humps 56 reside outside of the housing 20 and so do not resist any motion of the shuttle 40. When the slide 45 of the shuttle 40 has abutted the second end 34 of the tracks 30, the shuttle 40 can be rotated (about arrow B of FIGS. 9 and 10). Once this rotation is approaching 90° of rotation, the forward humps 56 pass through the rear slot 28 of the housing 20 and snap into the second dimples 38, holding the shuttle 40 in the deployed position. The strength with which the forward humps 56 reside within the second dimples 38 is preferably greater than the threshold force at which the filament 60 buckles. In this way, the shuttle 40 remains solidly in the deployed position during use of the instrument 10.

With particular reference to FIGS. 5 and 8-11, details of the filament 60 are described, according to this preferred embodiment. The filament 60 is an elongate flexible and resilient structure typically formed of a homogeneous material having well understood mechanical properties, and particularly a desirable modulus of elasticity, elastic limit, ultimate strength and other material strength and flexibility characteristics.

The filament 60 has a width significantly less than a length of the filament 60, so that the filament 60 will function as a column when considered as a structural element. Columns are those structural elements which generally will fail under compression loads by buckling before failing by having compressing forces which exceed strength characteristics of the material. The filament 60 is preferably at least ten times longer than its width, and most typically approximately fifty to one hundred times longer than its width.

The filament 60 is preferably cylindrical in form with a circular cross-section that extends from a root 64 to a tip 66. The root 64 is coupled to the body 50 through a collar 62 which preferably extends from a portion of the slide 45. This collar 62 acts as a coupling device to secure the root 64 of the filament 60 rigidly to the shuttle 40 without rotation or translation of the filament 60 relative to the shuttle 40. The collar 62 is also formed such that it extends from the slide 45 enough to prevent damage to the filament 60. The form of the collar 62 and front slot 26 are also made such that the buckling of the filament 60 during operation does not interfere, in any way, with the housing 20. The filament 60 can be formed of a fiberglass type composite material or from a metal such as nickel titanium, or from a plastic material having suitable performance characteristics.

Of primary importance for the filament 60 is that it is sufficiently resilient that it can undergo buckling failure when axial loads are applied to the filament 60 greater than a threshold force, and with the filament 60 resiliently returning to an original position when these forces are removed. In particular, the filament 60 is provided from a material which has an elastic limit which is higher than the force at which the filament 60 is caused to undergo buckling failure.

Furthermore, the filament 60 is preferably sufficiently flexible and elastic that the filament 60 exerts a maximum force right before buckling, and then exerts a lesser axial force after buckling. In this way, the filament 60 can be pressed against the skin (e.g. the finger F of FIG. 11) and exert a maximum force immediately before buckling of the filament 60. After such buckling of the filament 60, forces applied to the finger F again decrease. Thus, a maximum force which can be applied by the filament 60 to the finger F is the buckling force (also called threshold force) for the filament 60. This buckling force is the force at which the filament 60 will undergo buckling failure when an axial load of that magnitude is applied to the filament 60. The individual thus receives a force (or pressure) matching this threshold force, each time it is used and consistent repeatable evaluation of nerve sensitivity can occur.

Buckling of the filament 60 can also be referred to as bending of the filament 60. As depicted in FIG. 11, such buckling typically involves the filament 60 transitioning from a linear form to a curving bent form by movement of a midportion of the filament 60 laterally (along arrow C of FIG. 11). As an alternative, the filament 60 would not necessarily have to have an initial entirely linear form and could still undergo buckling failure.

In use and operation, and with particular reference to FIGS. 1-4 and 6-11, details of the operation of the instrument 10 are described, according to this preferred embodiment. Initially, the shuttle 40 is positioned so that the filament 60 is retracted within the interior chamber 25 of the instrument 10 (FIGS. 1 and 8). When the instrument 10 is to be used, a user engages the lever 52 of the body 50 to cause the shuttle 40 to translate linearly with the slide 45 moving along the track 30 within the interior chamber 25 of the housing 20 (along arrow A of FIGS. 2 and 9). Such linear translation of the shuttle 40 continues until the slide 45 abuts the second end 34 of the tracks 30.

The shuttle 40 is then rotated (along arrow B of FIGS. 3, 4, 9 and 10). Such rotation continues until the filament 60 extends substantially perpendicular to the tracks 30 and the long axis of the housing 20, has rotated typically approximately 90°. The shuttle 40 and associated filament 60 are now in a deployed position.

The instrument 10 is then brought close to skin of an individual to be tested and the tip 66 of the filament 60 is caused to touch the skin of the individual and then a force is applied axially from the housing 20 to the tip 66 axially along the filament 60 until the filament 60 buckles. Typically, the user will then ask the individual "did you feel that?" or some other query to determine whether or not the individual has sufficient sensory perception of a tactile nature to feel the force applied by the instrument 10. The instrument 10 is then typically moved to a new site and another test is performed.

When the instrument 10 is no longer needed, the shuttle 40 and associated filament 60 are retracted by reversing the step described above. The instrument 10 can then be stored without concern for damaging the filament 60 until the instrument 10 again needs to be used.

With particular reference to FIGS. 12-22, details of an alternative second embodiment instrument 110 are described. This alternative instrument 110 defines an alternative embodiment of the instrument 10 of the preferred embodiment. This alternative instrument 110 is similar in many respects to the instrument 10 with corresponding parts generally having similar part reference numbers except with the addition of "100" to each part number.

Thus, the alternative instrument 110 includes an elongate housing 120 extending from a proximal end 122 to a distal end 124. An interior chamber 125 is located within the housing 120 which is accessed through a front slot 126 and a rear slot 128. Notches 129 are formed in the rear slot 128.

A track 130 is formed within the interior chamber 125 of the housing 120. This track 130 is in the form of recesses formed in side walls of the interior chamber 125. The track 130 extends from a first end 132 to a second end 134. Uniquely, the track 130 of the alternative instrument 110 includes a curve 135 between the first end 132 and the second end 134, and very close to the second end 134. This curve 135 preferably is a 90° curve. The second end 134 is also uniquely preferably squared off rather than rounded in the case of the tracks 30 of the instrument 10 of the first embodiment. The interior chamber 125 preferably also includes a first dimple pair 136 and a second dimple pair 138 similar to the dimples 36, 38 of the preferred embodiment.

A shuttle 140 is provided with the alternative instrument 110 which includes a slide 145, a body 150 and a filament 160. The shuttle 140 defines a second portion of the alternative instrument 110 separate from the housing 120. The slide 145 uniquely includes a flat face 146 on one side thereof and a cylindrical surface 147 on another side thereof. The slide 145 includes flat ends 149 on opposite lateral sides of the slide 145. The flat face 146 is provided so that it can abut the flat second end 134 of the track 130 and help to hold the shuttle 140 and associated filament 160 without rotation, when the shuttle 140 and filament 160 are in a fully deployed position.

The body 150 includes a lever 152 which preferably includes a ramp 153 on an end thereof and which is angled relative to the otherwise generally flat lever 152. The ramp 153 helps to cause the shuttle 140 to rotate with the slide 145 passing through the curve 135 in the track 130 by the user pushing lightly on the ramp 153 when the shuttle 140 has been moved close to the deployed position for the shuttle 140 and associated filament 160. Such pushing of the ramp 153 helps to route the slide 145 in a curving fashion along the curve 135 of the track 130 to push the shuttle 140 fully to the deployed position.

The body 150 further includes a peripheral edge 154 with lateral sides 155 generally parallel and spaced from each other defining a generally constant width for the body 150. The body 150 includes a forward hump pair 156 and rearward hump pair 158. The humps 156, 158 are generally similar to the humps 56, 58 of the preferred embodiment and provide a similar function of holding the shuttle 140 either in the stored position or the deployed position. Positioning of the humps 156, 158 and dimples 136, 138 can be slightly adjusted as needed to accommodate differences between the instruments 10, 110.

The filament 160 is attached to the slide 145 through the collar 162. The filament 160 extends from a root 164 adjacent the collar 162 to a tip 166 opposite the root 164. The filament 160 is preferably similar to the filament 60 of the first embodiment.

Figures 21, 22:
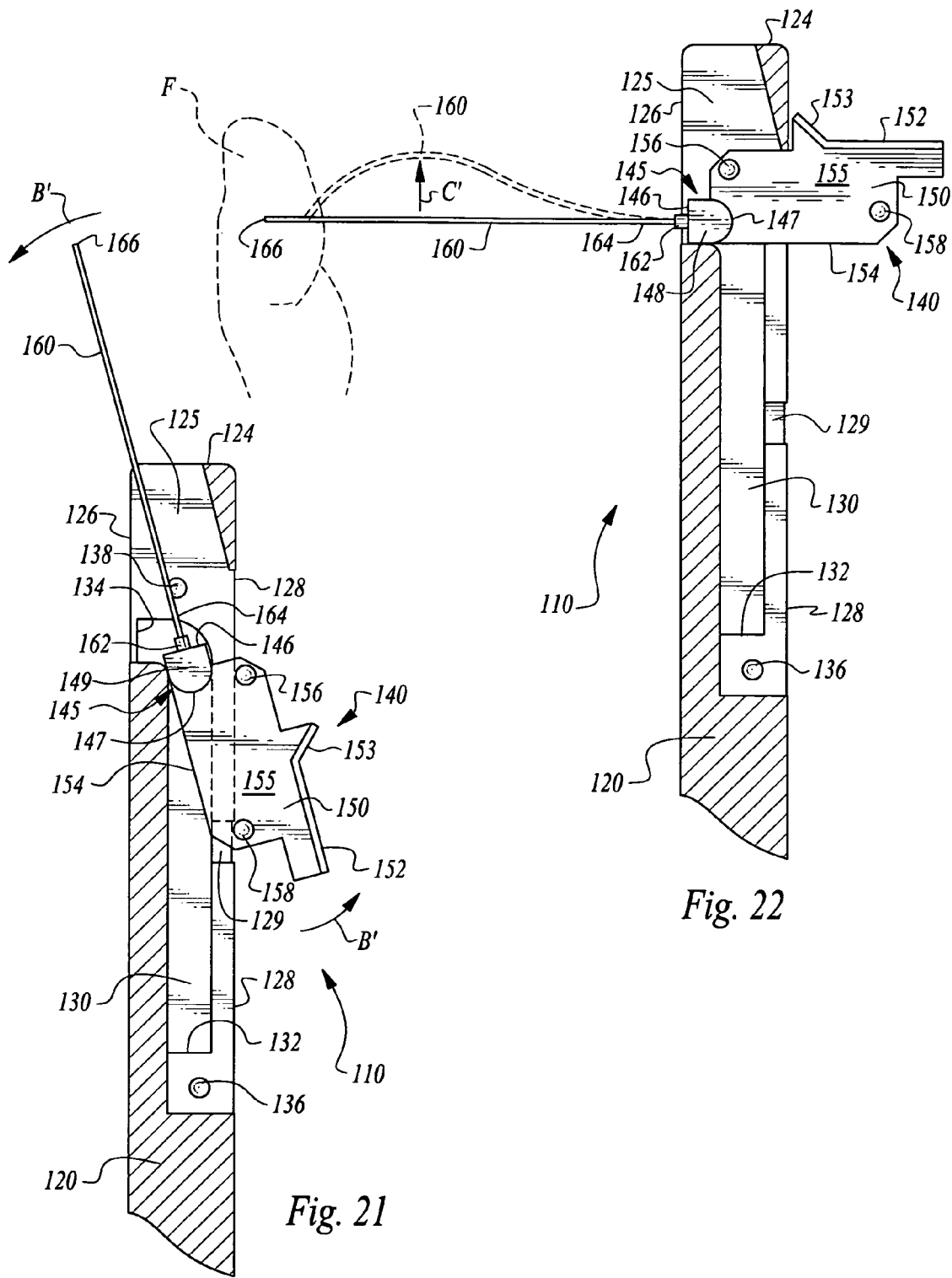

In use and operation, the alternative instrument 110 is generally used similar to the instrument 10 described above. Initially, the shuttle 140 and associated filament 160 are in a stored position (FIGS. 12 and 19). A user then places a finger on the lever 152 of the body 150 of the shuttle 140 and applies a force linearly and longitudinally along a long axis of the housing 120. This urges the shuttle 140 and associated slide 145 toward the distal end 124 of the housing 120 by movement of the slide 145 within the track 130 (along arrow A' of FIGS. 13 and 20). When the slide 145 reaches the curve 135, resistance to further linear motion is encountered. The user then applies a force against the ramp 153 of the lever 152 to help cause the slide 145 to rotate around the curve 135 (arrow B' of FIGS. 20 and 21), along with rotation of the shuttle 140 and included body 150 and filament 160. Such rotation of the shuttle 140 as the slide 145 passes about the curve 135 continues until this slide 145 abuts the second end 134 of the track 130 (FIGS. 15 and 22).

The shuttle 140 and associated filament 160 have thus been fully deployed. The instrument 110 is then utilized by bringing the filament 160 into contact with the individual, such as at a finger F. If the filament 160 buckles (motion along arrow C' of FIG. 22) a threshold force of standard amount has been applied. The individual is then queried to determine whether the individual could feel the force being applied. Data is then gathered as to the degree of sensory perception exhibited by the individual. When the instrument 110 is no longer to be utilized, the shuttle 140 and associated filament 160 are retracted by reversing of the steps described above until the filament 160 is again protected within the interior chamber 125 of the housing 120.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. An instrument for neurosensory evaluation, comprising in combination:
   an elongate housing;
   an elongate guide coupled to said housing;
   an elongate filament, said filament adapted to elastically buckle when compression loads above a buckling threshold are exceeded;
   a carrier, said filament coupled to said carrier;
   said carrier adapted to translate longitudinally along said elongate guide; and
   said carrier adapted to rotate to change an orientation of said filament relative to said housing.

2. The instrument of claim 1 wherein said carrier is adapted to pivot about a single point relative to said housing without simultaneous translation of said carrier.

3. The instrument of claim 1 wherein said carrier is adapted to travel along a curving path forming a portion of said elongate guide, said curving path adapted to cause said carrier to change an orientation of said filament when said carrier passes along said curving path.

4. The instrument of claim 1 wherein said elongate guide includes a track formed on said elongate housing, said carrier including a slide riding in said track as said carrier moves longitudinally along said track.

5. The instrument of claim 4 wherein said housing includes an interior chamber, said track located in walls of said interior chamber, at least portions of said carrier located within said chamber, said chamber including at least one slit adapted to accommodate deployment of said filament out of said interior chamber through said slit upon filament rotation relative to said housing.

6. The instrument of claim 5 wherein said guide includes at least two tracks formed on opposite walls of said interior chamber, said tracks in the form of elongate recesses in said walls of said interior chamber.

7. The instrument of claim 6 wherein said slide of said carrier includes a cylindrical wall with a diameter similar to a width of said groove forming said track.

8. The instrument of claim 7 wherein said tracks extend from a first end to a second end, said carrier adapted to pivot when said slide of said carrier is located at said second end of said track.

9. The instrument of claim 7 wherein said two tracks extend from a first end to a second end with a curve interposed between said first end and said second end, said carrier adapted to travel with said slide within said curve from said first end, along said curve and to said second end.

10. The instrument of claim 5 wherein said housing includes at least two slits extending into said interior chamber including a front slit and a rear slit, said front slit adapted to allow deployment of said filament out of said interior chamber upon filament rotation and said rear slit having at least portions of said carrier extending therethrough in the form of a manually engageable lever.

11. A nerve tactile sensitivity probe, comprising in combination:
   a housing;
   said housing having a hollow interior chamber;
   an elongate guide formed within said interior chamber;
   a carrier adapted to move along said elongate guide;
   said carrier including an elongate filament, said filament adapted to elastically buckle when compression loads above a buckling threshold are exceeded; and
   said carrier adapted to rotate to change an orientation of said filament relative to said housing.

12. The probe of claim 11 wherein said housing is elongate in form with a longitudinal dimension of said housing generally aligned with a longitudinal dimension of said elongate guide.

13. The probe of claim 11 wherein said elongate guide includes at least two tracks formed as recesses on opposite walls of said interior chamber.

14. The probe of claim 13 wherein said carrier includes a slide, said slide extending into each of said tracks to allow said carrier to slide along said tracks.

15. The probe of claim 14 wherein said slide has a circular form, said carrier adapted to pivot about a center point of said slide, for at least some positions of said carrier along said tracks.

16. The probe of claim 14 wherein said tracks include a curve between ends thereof, said slide of said carrier adapted to follow said curve to rotate said carrier along with said elongate filament included with said carrier.

17. The probe of claim 11 wherein said interior chamber has a size at least as large as said elongate filament, such that said filament can be contained entirely within said interior chamber when said filament is retracted.

18. A tool for testing skin nerve sensitivity, comprising in combination:
- an elongate housing;
- an elongate guide coupled to said housing;
- an elongate filament, said filament adapted to elastically buckle when compression loads above a buckling threshold are exceeded;
- a carrier, said filament coupled to said carrier;
- said carrier adapted to translate longitudinally along said elongate guide;
- wherein said elongate guide includes a track formed on said elongate housing, said carrier including a slide riding in said track as said carrier moves longitudinally along said track;
- wherein said housing includes an interior chamber, said track located in walls of said interior chamber, at least portions of said carrier located within said chamber, said chamber including at least one slit adapted to accommodate deployment of said filament out of said interior chamber through said slit; and
- wherein said guide includes at least two tracks formed on opposite walls of said interior chamber, said tracks in the form of elongate recesses in said walls of said interior chamber.

* * * * *